(12) United States Patent
Tyrell

(10) Patent No.: US 7,246,515 B2
(45) Date of Patent: Jul. 24, 2007

(54) FILTRATION TESTER

(75) Inventor: Paul Tyrell, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 109 days.

(21) Appl. No.: 11/080,052

(22) Filed: Mar. 15, 2005

(65) Prior Publication Data

US 2006/0207316 A1    Sep. 21, 2006

(51) Int. Cl.
*G01N 15/08* (2006.01)
(52) U.S. Cl. .......................................... 73/38
(58) Field of Classification Search .............. 73/38, 73/61.63
See application file for complete search history.

(56) References Cited

U.S. PATENT DOCUMENTS

| | | | |
|---|---|---|---|
| 4,815,313 A * | 3/1989 | Beard ........................ | 73/1.62 |
| 4,858,127 A * | 8/1989 | Kron et al. ................. | 73/54.09 |
| 5,685,991 A | 11/1997 | Degen et al. | |
| 6,463,790 B1 | 10/2002 | Chun | |
| 6,883,958 B2 * | 4/2005 | Mayer ........................ | 366/197 |
| 7,040,512 B2 * | 5/2006 | Tanny et al. ........... | 222/189.11 |
| 7,117,901 B2 * | 10/2006 | Martinell Gisper-Sauch et al. .............................. | 141/2 |
| 2003/0100125 A1 * | 5/2003 | Pressman et al. ........... | 436/177 |
| 2004/0174405 A1 | 9/2004 | Adachi et al. | |
| 2004/0206179 A1 | 10/2004 | Kamiyama | |

FOREIGN PATENT DOCUMENTS

EP            477973 A    *    4/1992

\* cited by examiner

*Primary Examiner*—Hezron Williams
*Assistant Examiner*—John Fitzgerald

(57) ABSTRACT

A filtration tester has a scale, a collector disposed on the scale, a pump having an outlet aligned with an opening of the collector, and a force sensor connected to the pump.

19 Claims, 5 Drawing Sheets

FILTRATION TESTER

BACKGROUND

When designing various systems or devices, such as fluid delivery systems, e.g., ink delivery systems, preliminary testing is often performed to determine how these systems or devices are going behave during operation, and to perhaps determine if or when certain failures may occur. For example, for ink delivery systems, it is important to investigate whether ink delivery nozzles will be come clogged or partially clogged over time, leading to reduced printing performance. In many cases, it may take impractical lengths of time to determine how a device or system will behave, especially well into the system's or device's lifecycle. Therefore, tests are often developed to be conducted for reduced times that simulate operation of a system or device over a much longer time.

DETAILED DESCRIPTION

In the following detailed description of the present embodiments, reference is made to the accompanying drawings that form a part hereof, and in which is shown by way of illustration specific embodiments that may be practiced. These embodiments are described in sufficient detail to enable those skilled in the art to practice disclosed subject matter, and it is to be understood that other embodiments may be utilized and that process, electrical or mechanical changes may be made without departing from the scope of the claimed subject matter. The following detailed description is, therefore, not to be taken in a limiting sense, and the scope of the claimed subject matter is defined only by the appended claims and equivalents thereof.

Figure 1:
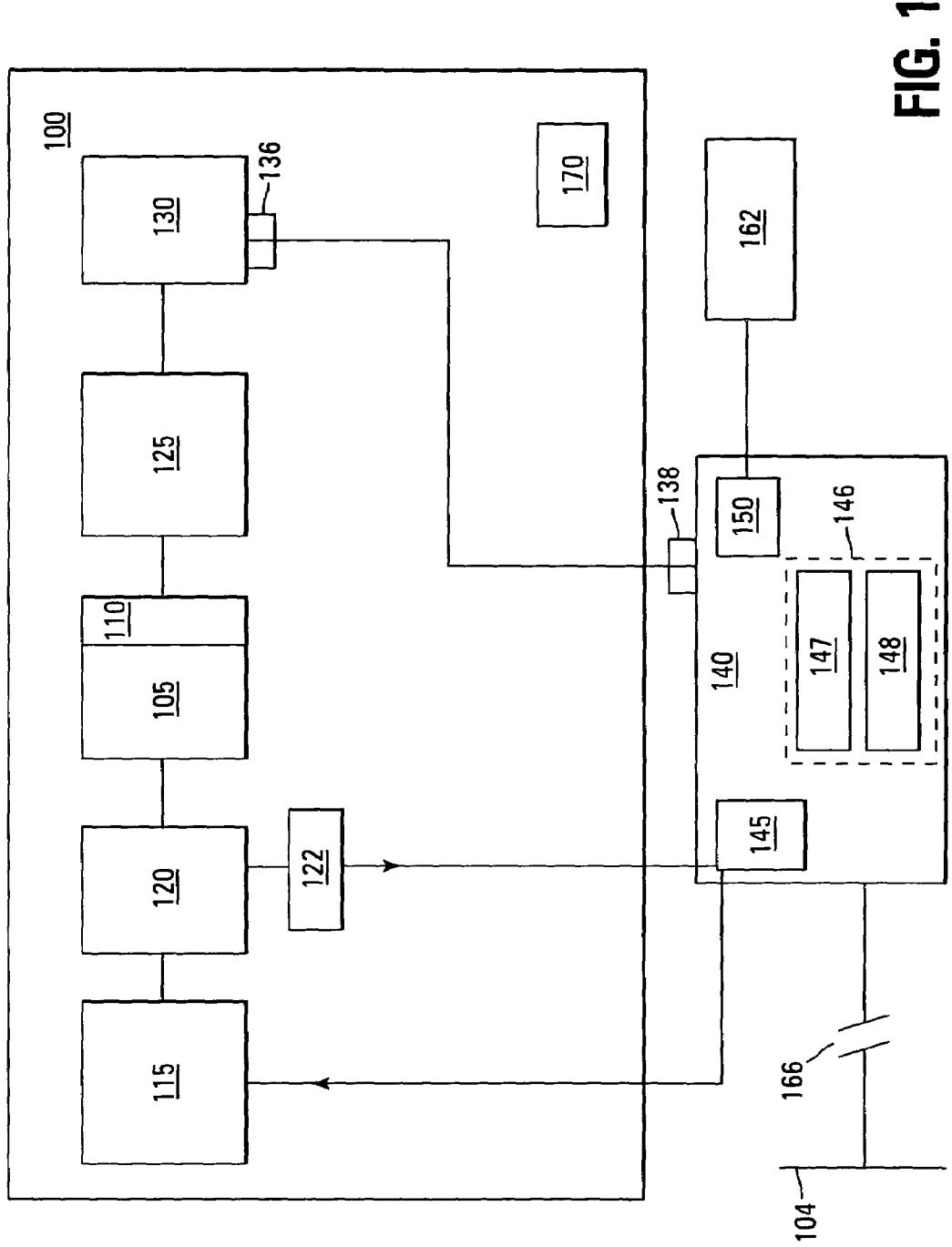
FIG. 1 is a block diagram of an embodiment of a filtration tester, according to an embodiment of the present disclosure.

FIG. 1 is a block diagram of a filtration tester 100, according to an embodiment. Filtration tester 100 includes a dispenser (or pump) 105, e.g., a syringe pump, adapted to receive a filter 110 for testing. The filter may be of glass, paper, metal or plastic, have various pore sizes, and have various constructions. An actuator 115 actuates pump 105. For a syringe pump, actuator 105 is an air-activated piston disposed in an air cylinder. A force sensor 120, e.g., a load cell, is used to determine the force applied to a liquid, e.g., ink, as it is pumped by pump 105 through filter 110 and into a collector 125. Collector 125 is disposed on a scale 130 that measures the mass of liquid that flows through the filter 110 and into collector 125 at a plurality of time instants.

For one embodiment scale 130 has a data output port 136, e.g., an RS-232 port, coupled to a data input port 138, e.g., RS-232 port, of a controller (or computer) 140 that for another embodiment, is a personal computer. For various embodiments computer 140 may be external to tester 100 or an integral component of tester 100. A data output of force sensor 120 is also coupled to computer 140. An input of actuator 115 is coupled to an output of computer 140 for receiving inputs therefrom based on inputs to computer 140 from scale 130. For another embodiment, force sensor 120 and actuator 115 interface with computer 140 via a data acquisition board 145 within computer 140. For some embodiments, scale 130 may connect to data acquisition board 145. For another embodiment, the output of force sensor 120 is amplified using an amplifier 122 disposed between force sensor 120 and computer 140. For another embodiment, a DC power supply 170 powers force sensor 120, scale 130, and regulation of actuator 115.

For one embodiment, computer 140 has a user interface 146 that includes a display device 147, such as a monitor, and a user input device 148, such as a keyboard. For some embodiments, user input device 148 may be a portion of display device 147 in the form of soft-touch keys. A printer 162 may be connected to computer 140 for one embodiment and for another embodiment may be an integral component of tester 100. For one embodiment, computer 140 is adapted to transmit data corresponding to a data network 164 via an interface 166. For one embodiment, data network 164 is a Local Area Network (LAN), the Internet, or the like, and interface 166 is a network adaptor (or network interface card).

For another embodiment, computer 140 is adapted to perform methods in accordance with embodiments of the present disclosure in response to computer-readable instructions. These computer-readable instructions are stored on a computer-usable media 150 of computer 140 and may be in the form of software, firmware, or hardware. In a hardware solution, the instructions are hard coded as part of a processor, e.g., an application-specific integrated circuit (ASIC) chip, a field programmable gate array (FPGA), etc. In a software or firmware solution, the instructions are stored for retrieval by computer 140. Some additional examples of computer-usable media include static or dynamic random access memory (SRAM or DRAM), read-only memory (ROM), electrically-erasable programmable ROM (EEPROM or flash memory), magnetic media and optical media, whether permanent or removable.

Figure 2:
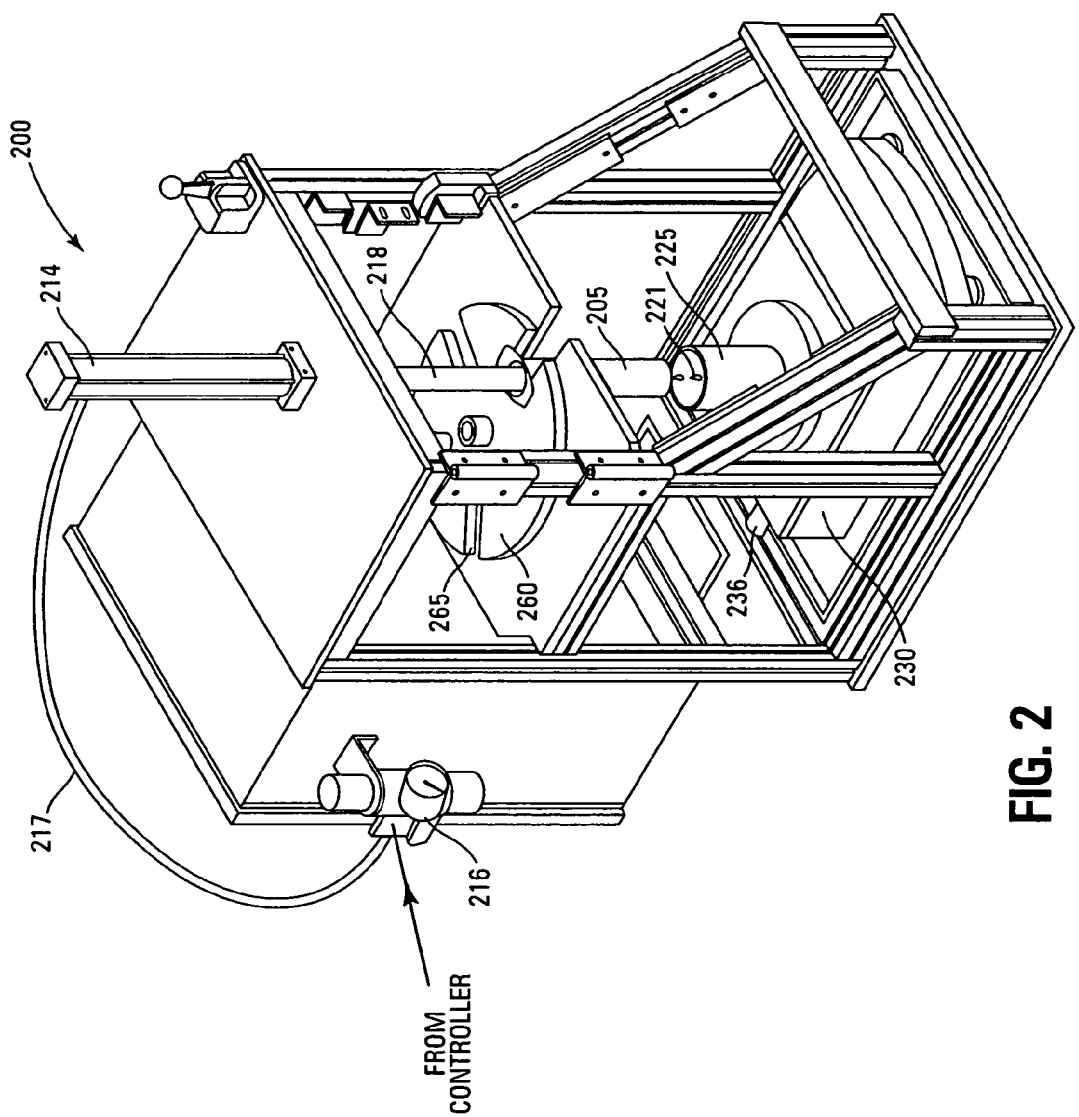
FIG. 2 is a front isometric view of an embodiment of a filtration tester, according to another embodiment of the present disclosure.

FIG. 2 is a front isometric view of a filtration tester 200, according to another embodiment. Filtration tester 200 includes a syringe pump 205 that is shown in more detail in FIG. 3, according to another embodiment. A filter 210 formed integrally with a housing 212, for one embodiment, is removably attached to an exit of syringe pump 205, e.g., by threading, to be tested. For one embodiment, filter 210 is a commercially available syringe filter.

Figure 3:
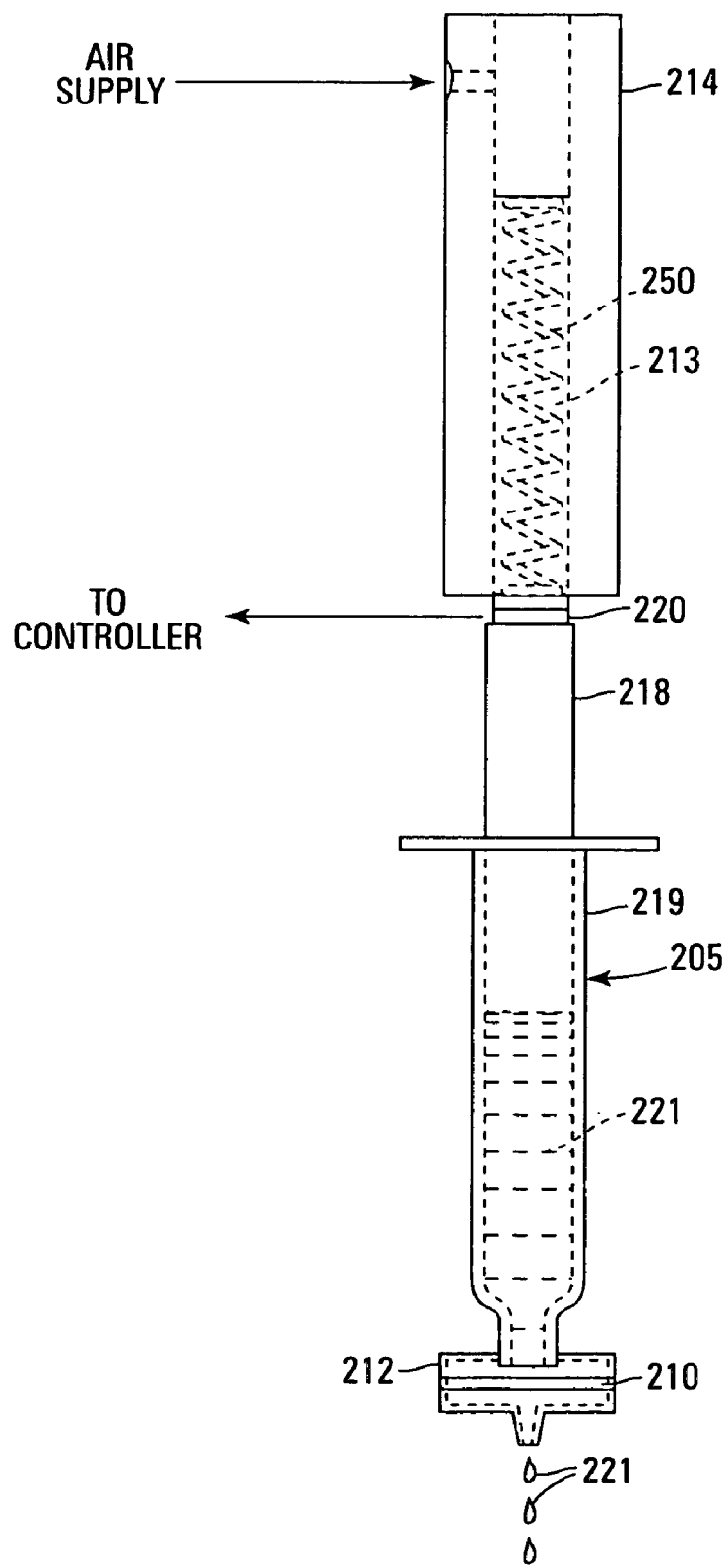
FIG. 3 is a detailed view of an embodiment of a syringe pump of an embodiment of a filtration tester, according to another embodiment of the present disclosure.

An air-activated piston 213 disposed in an air cylinder 214 (FIGS. 2 and 3) actuates syringe pump 205 when air flows into to air cylinder 214, via a tube 217 (FIG. 2) from an air regulator 216 that can be electrically controlled using control signals from a computer, such as computer 140 of FIG. 1. The air causes piston 213 to extend from cylinder 214 into engagement with a plunger 218 of syringe pump 205. Extending piston 213 moves plunger 218 into a barrel 219 of syringe pump 205. Plunger 218 in turn pushes against a liquid 221 e.g., ink, within barrel 219 and pushes liquid 221 through filter 210 so that it exits housing 212, as shown in FIG. 3. For one embodiment, a biasing device 250, such as a spring, is connected to piston 213 for biasing piston in a retracted position within cylinder 214. That is, biasing device 250 retracts piston 213 when the air pressure thereon is sufficiently reduced or removed.

A load cell 220 is disposed between piston 213 and plunger 218, as shown in FIG. 3, and is used to determine the force applied to plunger 218 by piston 213 and thus the force applied to liquid 221. Load cell 220 is coupled to a computer, such as computer 140 of FIG. 1, for sending output signals thereto.

The liquid 221 flows through an open top of a collector (or cup) 225 after passing through filter 210 (FIG. 2). Collector 225 is disposed on a scale 230 that includes a data port 236, such as an RS-232 port, that is coupled to a computer, such as computer 140 of FIG. 1. Scale 230 measures the mass of liquid that flows through the filter 210 and into collector 225 at a plurality of time instants.

For another embodiment, filtration tester 200 is adapted to receive syringe pumps of different sizes. For one embodiment, a turret 260 accomplishes this. Specifically, turret 260 includes a plurality of slots 265 respectively sized to receive different sized syringe pumps. Rotating turret 260 so a portion of a slot 265 aligns with collector 225 selects that slot 265, as shown in FIG. 2.

For one embodiment, tester 200 operates in a substantially constant-force (or constant-pressure) mode of operation. During the constant-force mode, the pressure applied to syringe pump 205 is maintained a substantially fixed preselected value. For one embodiment, the user inputs this pressure via the computer, e.g. in response to a prompt from the computer. For another embodiment, the computer prompts the user to input the air pressure, and then instructs air regulator 216 to set that pressure in response to the input. For some embodiments, the computer monitors the force on the load cell. If the force exceeds a predefined upper control limit or drops below a predefined lower control limit, the computer instructs air regulator 216 (FIG. 2) to respectively decrease or increase the pressure to bring the force measured by the load cell back within the control limits. The applied force causes liquid 221 to flow though filter 210 and into collector 225 (FIG. 2), and the computer receives signals from scale 230 representative of the instantaneous mass in the collector at a plurality of sample times. For one embodiment, the user inputs the duration of the sample times, i.e. the sample rate, into the computer, e.g., in response to a prompt from the computer.

For another embodiment, tester 200 operates in a substantially constant-mass-rate mode of operation. That is, the mass flow rate through the filter is maintained substantially constant. For one embodiment, the user inputs the desired mass flow rate into the computer, e.g., in response to being prompted by the computer. After the desired mass flow is entered into the computer, the computer instructs air regulator 216 (FIG. 2) to set the nominal pressure for attaining that mass flow rate for one embodiment. For some embodiments, the user may be prompted for test profile data characterizing a particular test run, such as the filter type, filter pore size, filter construction, control liquid type, if control liquid is used, a user identification, sample rate, test identification, an destination address on a data network to which test results can be sent, etc., before starting a test run.

The nominal pressure causes syringe pump 205 to expel liquid through filter 210 and into collector 225 (FIG. 2). Scale 230 sends signals indicative of the collected mass at two or more sample times to the computer, and the computer determines the mass flow rate, e.g., from the amount of mass collected for during given sample time interval. If the mass flow rate exceeds a predefined upper control limit or is below a predefined lower control limit, the computer instructs air regulator 216 (FIG. 2) to respectively decrease or increase the pressure to bring the mass flow rate within the control limits.

For some embodiments, when syringe pump 205 is empty, the signals the computer receives from scale 230 indicate that the mass in collector 225 is no longer changing. In response, the computer instructs air regulator 216 to turn off the air, and biasing device 250 retracts piston 213. For another embodiment, when signals the computer receives from scale 230 indicate that the change in the mass in collector 225 is below a predetermined threshold, the computer determines that syringe pump 205 is empty or that the filter is clogged. For one embodiment, this is indicative of an end point of a test run, and the computer instructs air regulator 216 to turn off the air, and biasing device 250 retracts piston 213.

Figure 4:
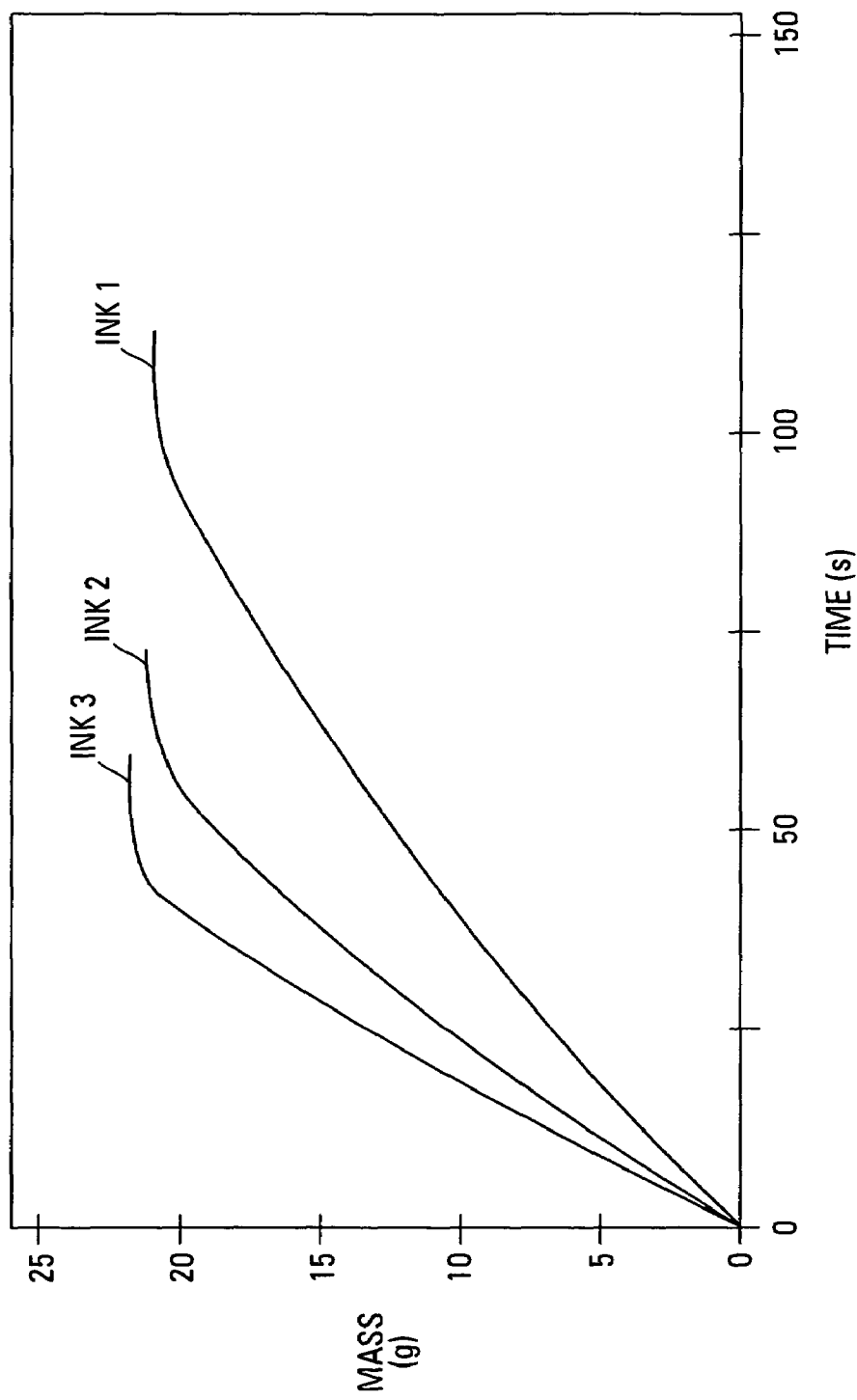
FIG. 4 presents exemplary data for flows through a filter, according to another embodiment of the present disclosure.

FIG. 4 presents exemplary filtration data for three different inks obtained from operating filtration tester 200 in the constant-force mode, according to an embodiment. Note that ink 1 filters the slowest, with ink 2 filtering faster than ink 1, and ink three filtering slightly faster than ink 2.

Figure 5:
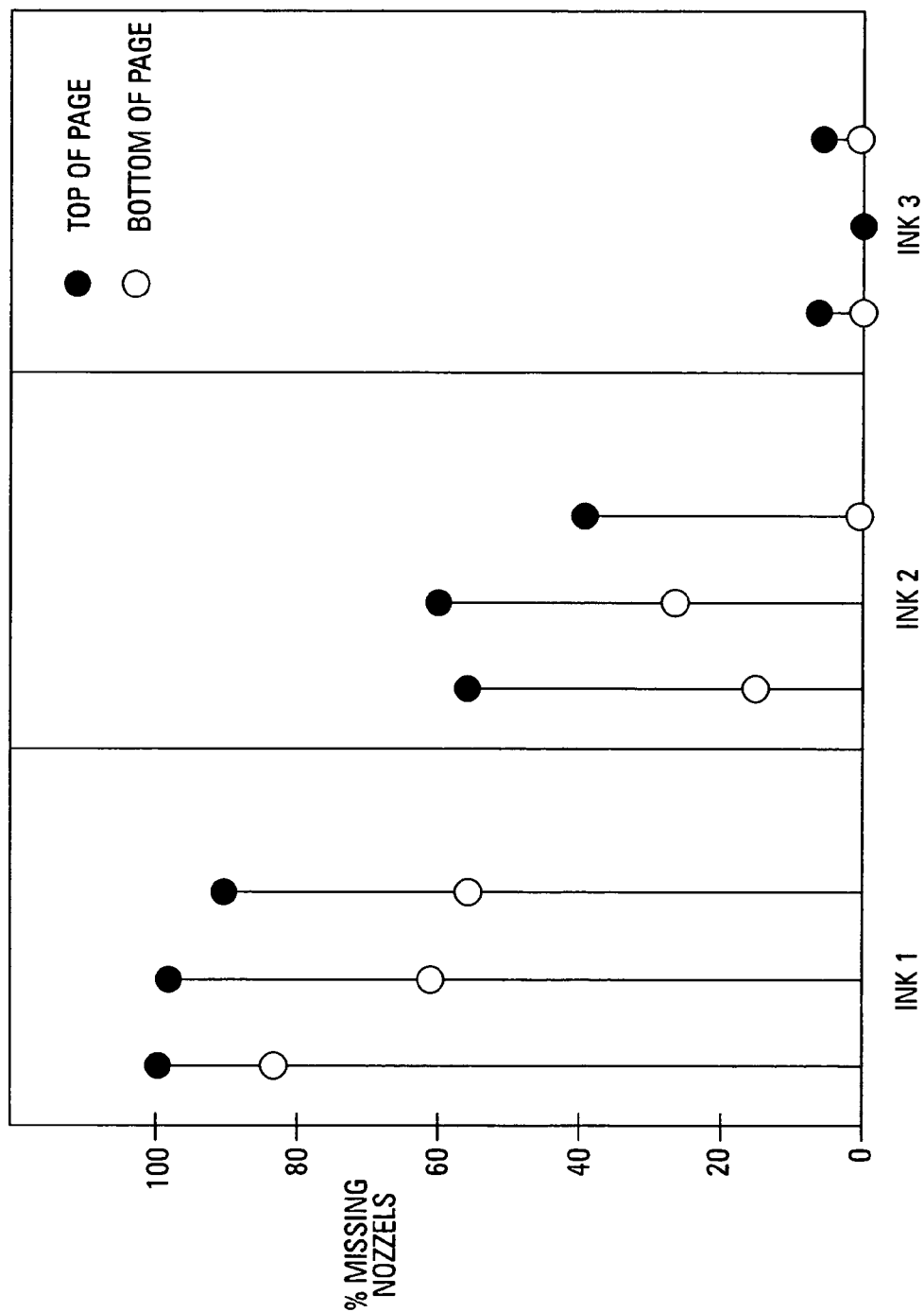
FIG. 5 presents exemplary nozzle performance data, according to another embodiment of the present disclosure.

The filtration data of FIG. 4 can be linked to the performance (or health) of ink ejection nozzles of an ink ejection device, such as an ink-jet print head. This is illustrated in FIG. 5, according to another embodiment. FIG. 5 presents nozzle performance as a percentage of the total nozzles that are missing (or inoperative) for the inks of FIG. 4. The closed data symbols correspond to the nozzle performance during printing at the top of a page, while the open data symbols correspond to the nozzle performance during printing at the bottom of the page. Moreover, printing at the top of the page, for one embodiment, occurred immediately after the nozzles were removed from a simulated storage condition corresponding to a capped state of the nozzles. It is seen that nozzle performance of FIG. 5 correlates with the filtration data of FIG. 4. That is, the largest number of missing nozzles both at the top and bottom of the page occurs for ink 1 that had the lowest filtration rates. The higher filtration rates of inks 2 and 3 in FIG. 4 are reflected in the increased nozzle performance (i.e., fewer missing nozzles) in FIG. 5. For some embodiments, multiple inks may be tested using filtration tester 200, and the computer may compare the filtration data of the respective inks and indicate which ink will result in better nozzle performance based on the comparison.

The simulated storage condition, for one embodiment, was accomplished by placing the inks and nozzles in a heated chamber, where the heat acts to accelerate the storage time. However, four weeks, was required to obtain the performance data of FIG. 5. Note that the filtration data of FIG. 4 infers the performance data of FIG. 5 and can be obtained, for this example, in less than one day.

CONCLUSION

Although specific embodiments have been illustrated and described herein it is manifestly intended that the scope of the claimed subject matter be limited only by the following claims and equivalents thereof.

What is claimed is:

1. A filtration tester comprising:
   a scale;
   a collector disposed on the scale;
   a pump having an outlet aligned with an opening of the collector; and
   a force sensor connected to the pump.

2. The filtration tester of claim 1, wherein the pump is a syringe pump.

3. The filtration tester of claim 1, wherein the scale comprises a data port.

4. The filtration tester of claim 1 wherein the scale and the force sensor are connectable to a computer.

5. The filtration tester of claim 1, wherein the force sensor is a load cell.

6. The filtration tester of claim 1, wherein the pump is adapted to receive a filter at the outlet thereof.

7. The filtration tester of claim 1 further comprises an actuator for actuating the pump.

8. The filtration tester of claim 1 further comprises a controller connected to the scale and the force sensor.

9. The filtration tester of claim 8, wherein the controller comprises a user interface.

10. The filtration tester of claim 8 further comprises a printer connected to the controller.

11. A filtration tester comprising:
   a scale;
   a collector disposed on the scale;
   a syringe pump having an outlet aligned with an opening of the collector;
   a cylinder containing a piston attached to a plunger of the syringe pump; and
   a load cell disposed between the piston and the plunger of the syringe pump.

12. The filtration tester of claim 11, wherein the scale and the load cell are connectable to a computer.

13. The filtration tester of claim 11, wherein the cylinder is connectable to an air supply.

14. The filtration tester of claim 11 further comprises an air regulator connected to the cylinder.

15. The filtration tester of claim 14, wherein the air regulator is electrically connectable to a computer.

16. A filtration tester comprising:
   a scale;
   a collector disposed on the scale;
   a syringe pump having an outlet aligned with an opening of the collector;
   a cylinder containing a piston attached to a plunger of the syringe pump;
   an air regulator connected to the cylinder;
   a load cell disposed between the piston and the plunger of the syringe pump; and
   a controller connected to the scale, load cell, and air regulator.

17. The filtration tester of claim 16, wherein the controller comprises a user interface.

18. The filtration tester of claim 16, wherein the controller is connectable to a data network.

19. The filtration tester of claim 16 further comprises a printer connected to the controller.

* * * * *